(12) United States Patent
Ho et al.

(10) Patent No.: US 9,745,252 B2
(45) Date of Patent: Aug. 29, 2017

(54) CROSS-LINKING MOIETY

(75) Inventors: Peter Ho, Singapore (SG); Lay-Lay Chua, Singapore (SG); Richard Henry Friend, Singapore (SG); Jie-Cong Tang, Singapore (SG); Rui-Qi Png, Singapore (SG); Bibin Thomas Anto, Singapore (SG); Perq-Jon Chia, Singapore (SG); Zhi Kuang Tan, Singapore (SG); Kim Kian Choo, Singapore (SG)

(73) Assignee: NATIONAL UNIVERSITY OF SINGAPORE, Singpore (SG)

( * ) Notice: Subject to any disclaimer, the term of this patent is extended or adjusted under 35 U.S.C. 154(b) by 75 days.

(21) Appl. No.: 13/513,702

(22) PCT Filed: Dec. 6, 2010

(86) PCT No.: PCT/SG2010/000454
§ 371 (c)(1),
(2), (4) Date: Jun. 4, 2012

(87) PCT Pub. No.: WO2011/068482
PCT Pub. Date: Jun. 9, 2011

(65) Prior Publication Data
US 2012/0244294 A1 Sep. 27, 2012

Related U.S. Application Data (60) Provisional application No. 61/266,561, filed on Dec. 4, 2009.

(51) Int. Cl.
*B05D 3/02* (2006.01)
*C07C 247/18* (2006.01)
(Continued)

(52) U.S. Cl.
CPC .......... *C07C 247/18* (2013.01); *C09D 201/04* (2013.01); *C08K 5/0025* (2013.01); *C08K 5/28* (2013.01)

(58) Field of Classification Search
CPC ... C07C 247/16; C07C 247/18; C09D 201/04; C08K 5/0025; C08K 5/28
(Continued)

(56) References Cited

U.S. PATENT DOCUMENTS

| 4,608,333 A | * | 8/1986 | Ohbayashi et al. | 430/281.1 |
| 2009/0004402 A1 | | 1/2009 | Ho et al. | 427/510 |

FOREIGN PATENT DOCUMENTS

| WO | WO 03/095586 | 11/2003 | C09K 11/06 |
| WO | WO 2004/100282 | 11/2004 | H01L 51/30 |
| WO | 2009068884 A1 | 6/2009 | |

OTHER PUBLICATIONS

Supplementary European Search Report dated Apr. 6, 2013.
(Continued)

*Primary Examiner* — Robert S Walters, Jr.
(74) *Attorney, Agent, or Firm* — Michael W. Ferrell; Ferrells, PLLC; Anna L. Kinney (57) ABSTRACT

A cross-linking moiety having a general formula I: $Ar_F$-W, wherein $Ar_F$ comprises a fluorinated phenyl azide group having at least one non-fluorine substituent that is bulkier than fluorine at a meta position relative to the azide group, and W comprises an electron-withdrawing group.

20 Claims, 1 Drawing Sheet (51) Int. Cl.
 *C09D 201/04* (2006.01)
 *C08K 5/00* (2006.01)
 *C08K 5/28* (2006.01)

(58) Field of Classification Search
 USPC .......................................................... 552/8
 See application file for complete search history.

(56) References Cited

OTHER PUBLICATIONS

Keivandidis, P.E. et al., "All-Solution Based Device Engineering of Multilayer Polymeric Photodiodes: Minimizing Dark Current", Applied Physics Letters. Apr. 30, 2009. 94, 173303.

Khong, S-H. et al., "General Photo-Patterning of Polyelectrolyte Thin Films via Efficient Ionic Bis(Fluorinated Phenyl Azide) Photo-Crosslinkers and Their Post-Deposition Modification", Advanced Functional Materials, 2007, vol. 17. pp. 2490-2499.

Chemical Abstracts Accession No. 2001:526050 and CAS Registry File: RN 350488-36-7, RN 350488-37-8 & RN 350488-38-9.

Keivandidis, P.E. et al., "All-Solution Based Device Engineering of Multilayer Polymeric Photodiodes: Minimizing Dark Current", Applied Physics Letters, Apr. 30, 2009, 94, 173303.

Khong, S-H. et al., "General Photo-Patterning of Polyelectrolyte Thin Films via Efficient Ionic Bis(Fluorinated Phenyl Azide) Photo-Crosslinkers and Their Post-Deposition Modification", Advanced Functional Materials, 2007, vol. 17, pp. 2490-2499.

International Search Report and Written Opinion of the International Searching Authority, Jan. 31, 2011.

Written Opinion of the International Preliminary Examining Authority, Jan. 9, 20012.

International Preliminary Report on Patentability, Jan. 31, 2011.

* cited by examiner

CROSS-LINKING MOIETY

CLAIM FOR PRIORITY

This application is based on International Application No. PCT/SG2010/000454 filed Dec. 6, 2010 which claimed priority to U.S. Provisional Application No. 61/266,561 filed Dec. 4, 2009. The priorities of these applications are hereby claimed and their disclosures incorporated herein by reference.

FIELD OF THE INVENTION

The present invention relates to a cross-linking moiety. In particular, the cross-linking moiety may be used in semiconductive layers in device manufacture.

BACKGROUND OF THE INVENTION

The development of high-quality polymer semiconductor heterostructures is crucially needed to the further improve the performance of polymer semiconductor devices. In light-emitting diodes for example, heterostructures are central for efficient charge-carrier injection and confinement, and also for control over their recombination, and the fate of the excitons generated. However this important goal has been hindered in the past by the lack of a sufficiently general cross-linking system that is suitable for cross-linking polymer semiconductors without degrading their charge-carrier transport and exciton properties.

Various methods involving the use of specific cross-linking chemistry have been proposed such as epoxy or oxetane ring-opening under acid-catalysis, or cycloaddition reactions. In a specific cross-linking reaction, two functional groups react together in the presence of light or heat to give a cross-link.

However these specific cross-linking chemistries have several characteristics that may not be advantageous. First, they require a very high concentration of the cross-linking moieties to be present, typically well above 10 mol % of a typical polymer repeat unit, so that a high enough local concentration for the bimolecular reaction may take place since the two reacting moieties have to come into contact. Such high concentrations of the cross-linker moieties may alter the desired morphological characteristics of the polymer. Second, a significant fraction of these cross-linking moieties are unfortunately stranded and so do not form cross-links, because they cannot find a cross-linking partner in the time they are active. These cannot be removed subsequently and thus give rise to an electronically significant concentration traps for charges, particularly electrons, and for excitons.

To overcome these two limitations, the use of non-specific cross-linking chemistry through fluorinated phenyl azides has been proposed (WO 2004/100282). Fluorinated phenyl azides can be photolysed to nitrenes when exposed to 254 nm (i.e., deep UV light) that insert into unactivated CH bonds. However, some loss of performance due to electron trapping and exciton quenching occurs particularly at high cross-linker concentrations.

There is therefore a need for an improved cross-linking moiety which may be suitable for cross-linking polymer semiconductors.

SUMMARY OF THE INVENTION

The present invention seeks to address at least one of the problems above and provide an improved cross-linking moiety. In particular, the cross-linking moiety according to the present invention may be suitable for use with polymer semiconductor layers such as charge transport layers and light emitting layers of polymer devices. The cross-linking moiety according to any aspect of the present invention provides a cross-linking function without degrading the properties of the polymer it is cross-linked to, or the adjacent layer of polymer layer.

According to a first aspect, there is provided a cross-linking moiety having a general formula I:

$$Ar_F\text{-W} \qquad (I),$$

wherein $Ar_F$ comprises a fluorinated phenyl azide group having at least one non-fluorine substituent that is bulkier than fluorine at a meta position relative to the azide group, and W comprises an electron-withdrawing group.

According to a particular aspect, the cross-linking moiety may be selected from the group consisting of: 4-azido-2-R-6-R'-3,5-difluorophenyl-1-W; 4-azido-2-R-3,5,6-trifluorophenyl-1-W; 4-azido-1-R-6-R'-3,5-difluorophenyl-2-W; 4-azido-1-R'-6-R-3,5-difluorophenyl-2-W; 4-azido-1-R-3,5,6-trifluorophenyl-2-W; and 4-azido-6-R-1,3,5-trifluorophenyl-2-W, wherein each R and R' is the same or different and is a non-fluorine substituent that is bulkier than fluorine; and W comprises an electron-withdrawing group.

According to another particular aspect, the cross-linking moiety may have a general formula II:

$$(Ar_F\text{-W})_n L \qquad (II),$$

wherein each $Ar_F$ is the same or different and comprises a fluorinated phenyl azide group having at least one non-fluorine substituent that is bulkier than fluorine at a meta position relative to the azide group, W comprises an electron-withdrawing group, L comprises a linker group, and n is an integer greater than or equal to 2.

In particular, a cross-linking moiety may have the general formula (II) when two or more single cross-linking moieties are linked together by a linker group.

$Ar_F$ may comprise any suitable fluorinated phenyl azide group. According to a particular aspect, $Ar_F$ may comprise a substituted fluorinated phenyl azide. In particular, $Ar_F$ may comprise a substituted fluorinated phenyl azide group having two fluorine atoms at least of two ortho positions relative to the azide group, and at least one non-fluorine substituent that is bulkier than F at a meta position relative to the azide group.

The non-fluorine substituent may be any suitable substituent. For example, the non-fluorine substituent may be selected from a group consisting of a substituted or non-substituted: alkyl group, cycloalkyl group, alkoxy group and cycloalkoxy group. In particular, the non-fluorine substituent may be a substituted or unsubstituted alkyl group. The alkyl group may be a linear or branched alkyl group. The alkyl group may have an alkyl chain length of from 1 to 18 carbon atoms. For example, the alkyl group may comprise a methyl, ethyl, isopropyl, secondary butyl, tertiary butyl, hexyl, octyl group, or branched derivatives thereof. Even more in particular, the alkyl group may be isopropyl or tertiary butyl.

According to a particular aspect, W may be in the para position relative to the azide group. W may comprise any suitable electron-withdrawing group suitable for the purposes of the present invention. For example, W may comprise a sulphonyl group or a carbonyl group. For example, the carbonyl group may be in the form of a keto, ester or amide. In particular, the W may comprise an electron-withdrawing group selected from the group consisting of:

—CO—, —C(O)O—, —S(O)₂O—, —C(O)N—, and —S(O)₂N—. Even more in particular, W may comprise an ester group, i.e. —C(O)O— group.

L may comprise any suitable linker group. L may comprise a divalent or multivalent linker group. According to a particular aspect, L comprises a linker group which may be selected from a group consisting of substituted or unsubstituted: alkyldioxy, alkyltrioxy, alkyldiamide, alkyltriamide and dialkyltrioxy. In particular, L comprises a linker group which may be selected from the group consisting of: ethylenedioxy, ethylenediamide, diethylenetrioxy and 1,3,5-trioxycyclohexane.

According to a particular aspect, the cross-linking moiety according to the present invention may be selected from the group consisting of:
ethylene bis(4-azido-2,3,5-trifluoro-6-methylbenzamide);
dodecylene bis(4-azido-2,3,5-trifluoro-6-methylbenzoate);
ethylene bis(4-azido-2,3,5-trifluoro-6-isopropylbenzoate);
ethylene bis(4-azido-3,5-trifluoro-2,6-diisopropylbenzoate);
ethylene bis(4-azido-3,5-trifluoro-2,6-dihexylbenzoate);
diethyleneoxy bis(4-azido-3,5-trifluoro-2,6-diisopropylbenzoate);
diethyleneoxy bis(4-azido-2,3,5-trifluoro-6-isopropylbenzoate); and
diethyleneoxy bis(4-azido-3,5-trifluoro-2,6-dihexylbenzoate).

A second aspect of the present invention provides a solution comprising a cross-linking moiety as described above. The solution may further comprise a polymer or oligomer. Any suitable polymer or oligomer may be used for the purposes of the present invention. In particular, the polymer or oligomer may be a semiconductive polymer or oligomer. For example, the polymer or oligomer may be a high molecular weight polymer or oligomer. In particular, the polymer or oligomer may have a molecular weight greater than or equal to about 10000 Da.

According to a third aspect, there is provided a method for forming a polymer device comprising the steps of:
(a) depositing a solution comprising a polymer or oligomer and a cross-linking moiety on a substrate to form a layer; and
(b) curing the layer to form an insoluble cross-linked polymer.

The polymer or oligomer and the cross-linking moiety may be as described above.

The polymer device prepared from the method according to the present invention may be a polymer LED device, a polymer waveguide LED device, a polymer distributed Bragg reflector, a polymer microcavity LED device, a polymer FET device, a polymer photodetector and a polymer photovoltaic device.

Any suitable curing process may be used for the curing step. In particular, the cross-linking moiety may be sensitive to ultraviolet radiation having a wavelength in the range 200 nm to 400 nm. The curing may therefore comprise exposing the layer to UV radiation having a wavelength in the range 200 nm to 400 nm in an inert atmosphere.

The cross-linked polymer may be unconjugated, partially conjugated, substantially conjugated or fully conjugated. According to a particular aspect, the cross-linking moiety may be part of the main chain of the polymer or oligomer, or may be attached as a side chain to the polymer or oligomer.

The method according to the present invention may further comprise annealing the cross-linked polymer. The annealing may be carried out at any suitable temperature. For example, the annealing may be at 90° C. for a suitable period of time.

According to a fourth aspect of the present invention, there is provided a polymer device obtained by the method as described above.

DETAILED DESCRIPTION OF THE INVENTION

One of the underlying mechanisms that causes the loss of performance is due to a nitrene attack onto the π-conjugated backbone, and intermolecular charge transfer between the polymer and the fluorinated phenyl azide rings, promoted by an undesirable quadrupolar interaction.

The present invention therefore provides an improved cross-linking moiety which suppresses the quadrupolar interaction. In particular, the π-π interaction between electron-rich organic semiconductor devices and electron-poor fluorophenyl azides is suppressed, and cross-links are more favourably allowed at the alkyl side chains. The cross-linking moiety according to the present invention may have a high photocross-linking efficiency. In particular, the absorption coefficient, photo-speed and insertion yield are not adversely affected to any significant extent, thereby making the photocross-linking process considerably more compatible with the presence of excitons, electrons and holes in semiconductor devices. Therefore, the cross-linking moiety according to the present invention may be used with semiconductor layers, such as charge transport layers and light-emitting layers, of polymer devices with even lesser adverse effects.

According to a first aspect, the present invention provides a cross-linking moiety having a general formula I:

$$Ar_F\text{-}W \qquad (I)$$

wherein $Ar_F$ comprises a fluorinated phenyl azide group having at least one non-fluorine substituent that is bulkier than fluorine at a meta position relative to the azide group, and W comprises an electron-withdrawing group.

The cross-linking moiety may be a single fluorinated phenyl azide cross-linking moiety. In particular, the cross-linking moiety having formula (I) may be selected from the group consisting of: 4-azido-2-R-6-R'-3,5-difluorophenyl-1-W; 4-azido-2-R-3,5,6-trifluorophenyl-1-W; 4-azido-1-R-6-R'-3,5-difluorophenyl-2-W; 4-azido-1-R'-6-R-3,5-difluorophenyl-2-W; 4-azido-1-R-3,5,6-trifluorophenyl-2-W; and 4-azido-6-R-1,3,5-trifluorophenyl-2-W, wherein each R and R' is the same or different and is a non-fluorine substituent that is bulkier than fluorine; and W comprises an electron-withdrawing group.

According to another particular aspect, the cross-linking moiety may have a general formula II:

(Ar$_F$-W)$_n$-L           (II), wherein each Ar$_F$ is the same or different and comprises a fluorinated phenyl azide group having at least one non-fluorine substituent that is bulkier than fluorine at a meta position relative to the azide group, W comprises an electron-withdrawing group, L comprises a linker group, and n is an integer greater than or equal to 2.

According to a particular aspect, n may satisfy the valency of the linker group comprised in L.

In particular, two or more single cross-linking moieties may be linked together by any suitable linker group to give a cross-linking moiety having formula (II). In particular, two or more cross-linking moieties may be linked together by L through W.

Ar$_F$ may comprise any suitable fluorinated phenyl azide group. For the purposes of the present invention, a fluorinated phenyl azide group is defined as a phenyl azide group which has been substituted by at least one fluorine atom. In particular, in some embodiments a fluorine atom may be positioned in any positions that are ortho to the azide. In particular, Ar$_F$ may comprise a substituted fluorinated phenyl azide group having two fluorine atoms at least at two ortho positions relative to the azide group, and at least one non-fluorine substituent that is bulkier than F at a meta position relative to the azide group. According to a particular aspect, Ar$_F$ may comprise 3,5-difluorophenyl azide, 3,5,6-trifluorophenyl azide or 2,3,5-trifluorophenyl azide. Ar$_F$ may further comprise an electron-withdrawing group positioned para relative to the azide group. According to a particular aspect, Ar$_F$ may comprise a substituted 3,5-difluorophenyl-2W azide group, 3,5,6-trifluorophenyl-2W azide group or 1,5,6-trifluorophenyl-2W azide group.

The Ar$_F$ has at least one non-fluorine substituent that is bulkier than fluorine. For example, Ar$_F$ has one or two non-fluorine substituents. According to a particular aspect, Ar$_F$ comprises a fluorinated phenyl azide and may be substituted by one non-fluorine substituent at the meta position relative to the azide group. Even more in particular, Ar$_F$ comprises a fluorinated phenyl azide and may be substituted by two non-fluorine substituents at each meta position relative to the azide group. Each of the two non-fluorine substituents may be the same or different from each other.

A non-fluorine substituent that is bulkier than fluorine may be defined as a substituent which does not contain a fluorine atom and which is a chemical group that has a van der Waals radius which is larger than that of a fluorine atom, or equivalently, which has a van der Waals volume that is larger than that of a fluorine atom. Fluorine has an accepted van der Waals radius of about 1.5 Angstroms.

Any suitable non-fluorine substituent may be used for the purposes of the present invention. For example, the non-fluorine substituent may be selected from a group consisting of a substituted or non-substituted: alkyl, cycloalkyl, alkoxy and cycloalkoxy groups. In particular, suitable selection of the non-fluorine substituent comprises selecting such that the non-fluorine substituent does not interfere with the electron-withdrawing group.

In particular, the non-fluorine substituent may be a substituted or unsubstituted alkyl group. The alkyl group may be a linear or branched alkyl group. The alkyl group may have an alkyl chain length of from 1 to 18 carbon atoms. For example, the alkyl group may comprise a methyl, ethyl, isopropyl, secondary butyl, tertiary butyl, hexyl, octyl group or their branched derivatives. According to a particular embodiment, the alkyl group is a linear alkyl group. The linear chains of the alkyl group may solubilise more easily in a solution and promote further cross-linking of side chains of a polymer. Even more in particular, the alkyl group may be isopropyl or tertiary butyl.

According to a particular aspect, the non-fluorine substituent may be a substituted or unsubstituted cycloalkyl group. Any suitable cycloalkyl may be used for the purposes of the present invention. For example, the cycloalkyl group may comprise cyclohexyl and cyclopentyl.

According to a particular aspect, the non-fluorine substituent may be a substituted or unsubstituted alkoxy or cycloalkoxy group. Any suitable alkoxy or cycloalkoxy may be used for the purposes of the present invention. For example, the alkoxy group may comprise methoxy, ethoxy, propoxy, isopropoxy, hexoxy, oxtoxy, and their branched derivatives. For example, the cycloalkoxy may comprise cyclohexoxy.

The non-fluorine substituents do not cause an inductive electron-withdrawing effect as would a fluorinated substituent such as trifluoromethyl because the non-fluorine substituents according to the present invention allow the cross-linking moiety to donate electrons inductively into the Ar$_F$ ring so as to raise both the highest occupied molecular orbital (HOMO) and the lowest unoccupied molecular orbital (LUMO) energy levels. This has particular advantage to reduce electron trapping and exciton trapping due to the cross-linking moiety or its interaction with the semiconductive polymer.

W may comprise any suitable electron-withdrawing group for the purposes of the present invention. For example, W may comprise a sulphonyl group or a carbonyl group. The carbonyl group may be in the form of a keto, ester or amide. In particular, W may comprise an electron-withdrawing group selected from the group consisting of: —CO—, —C(O)O—, —S(O)$_2$O—, —C(O)N—, or —S(O)$_2$N—. Even more in particular, W may comprise an ester group, i.e. —C(O)O— group.

According to a particular aspect, W may be in the para position relative to the azide group.

L may comprise any suitable linker group for the purposes of the present invention. A linker group may be necessary when two or more cross-linking moieties are linked together. In particular, two or more cross-linking moieties may be linked together through W.

L may comprise a divalent (i.e. when n=2) or multivalent (i.e. when n is greater than 2) linker group. For example, L may comprise (CH$_2$)$_x$, where x is from 1 to 5, (CH$_2$)$_x$—O—(CH$_2$)$_x$, where x is from 1 to 3, or cyclohexadiyl segments. According to a particular aspect, L may comprise a linker group selected from a group consisting of substituted or unsubstituted: alkyldioxy, alkyltrioxy, alkyldiamide, alkyltriamide and dialkyltrioxy. In particular, L may comprise a linker group selected from the group consisting of: ethylenedioxy, ethylenediamide, diethylenetrioxy and 1,3,5-trioxycyclohexane.

According to a particular aspect, the cross-linking moiety according to the present invention may be selected from the group consisting of:

ethylene bis(4-azido-2,3,5-trifluoro-6-methylbenzamide);
dodecylene bis(4-azido-2,3,5-trifluoro-6-methylbenzoate);
ethylene bis(4-azido-2,3,5-trifluoro-6-isopropylbenzoate);
ethylene bis(4-azido-3,5-trifluoro-2,6-diisopropylbenzoate);
ethylene bis(4-azido-3,5-trifluoro-2,6-dihexylbenzoate);
diethyleneoxy bis(4-azido-3,5-trifluoro-2,6-diisopropylbenzoate);

diethyleneoxy bis(4-azido-2,3,5-trifluoro-6-isopropylbenzoate); and diethyleneoxy bis(4-azido-3,5-trifluoro-2,6-dihexylbenzoate).

The cross-linking moiety according to any aspect of the present invention may have many applications. For example, the cross-linking moieties may be used either mixed with a semiconductive polymer or as part of a polymer main chain or side chain, to form a cross-linked polymer product having a low concentration of cross-linked moieties. The low concentration of cross-linked moieties substantially does not degrade the performance of the polymer is a polymer device.

The cross-linking moiety may comprise two single cross-linking moieties which are linked together with a linker to give a cross-linkable additive that may be mixed in a solution state into a polymer to be cross-linked and deposited together with the polymer to form a homogeneously dispersed film. Upon photo-exposure, the cross-linkable additive cross-links two polymer chains together.

According to a particular aspect, two or more cross-linking moieties may be linked together by any suitable linker to give a cross-linkable additive. The linker may be as described above. In particular, two single cross-linking moieties may be linked together by a linker which may be substituted or unsubstituted: alkyldioxy, alkyldiamide or dialkyltrioxy units. Even more in particular, the linker may be ethylenedioxy, ethylenediamide or diethylenetrioxy units.

The cross-linking moiety may comprise three single cross-linking moieties which are linked together with a linker to give a cross-linkable additive that may be mixed in a solution state into a polymer matrix to be cross-linked and deposited together with the polymer to form a homogeneously dispersed film. Upon photo-exposure, the cross-linkable additive cross-links three polymer chains together.

For example, three or more cross-linking moieties may be linked together by any suitable linker to give a cross-linkable additive. The linker may be as described above. In particular, three single cross-linking moieties may be linked together by a linker which may be substituted or unsubstituted: alkyltrioxy or alkyltriamide units. Even more in particular, the linker may be 1,3,5-trioxycyclohexane units.

According to another particular aspect, the cross-linking moiety may comprise one $Ar_F$ group which is covalently bonded to an alkyl chain on a fraction of a monomer unit of a polymer chain. Upon photo-exposure, the $Ar_F$ group cross-links to an alkyl chain belonging to an adjacent polymer chain. In this way, the amount of cross-linking moieties may be reduced by a factor of two since one end of the cross-linking moiety is already attached to the monomer unit of the polymer. Since the cross-linking moiety is attached to the side chain, the impact on the optoelectronic properties of the polymer may be further reduced.

According to another particular aspect, the cross-linking moiety may comprise one $Ar_F$ group which may be linked to a functional group. The functional group may be a surface-energy modifier or a fluorescent group. For example, the functional group may be a perfluoroalkyl chain, wherein the alkyl chain has an alkyl chain length of from 4 carbon atoms, or a fluorescent dye. The cross-linking moiety may then be mixed into a polymer matrix to give controlled tension at the surface and interface. After photo-exposure, the cross-linking moiety is cross-linked and locked in place onto the polymer chain.

The cross-linking moiety according to any aspect of the present invention may have an absorption in the narrow transmission window in the deep ultraviolet (UV). The absorption may be in the range 200-400 nm. In particular, the range may be 200-300 nm, 245-275 nm, 250-260 nm. The absorption of a cross-linking moiety of the present invention may be measured by any suitable method. For example, the absorption may be measured by UV visible absorption spectroscopy.

It is preferable for the cross-linking moiety to have the appropriate absorption in the range above because this corresponds to a transition window common for a number of semiconductive polymers. Accordingly, cross-linking and imaging of the polymer may be accomplished at low exposure doses.

A second aspect of the present invention provides a solution comprising a cross-linking moiety according to any aspect of the present invention. The solution may further comprise a polymer or oligomer. The cross-linking moiety may be mixed with the polymer or oligomer in the solution or the cross-linking moiety may bind to the polymer or oligomer main chain or side chain.

Any suitable polymer or oligomer may be used for the purposes of the present invention. The polymer or oligomer may be soluble to form a solution with the cross-linking moiety. The polymer or oligomer may comprise a solubilising group. For example, the polymer or oligomer may comprise a solubilising group such as an alkyl, alkoxy aryl, cycloalkyl, aryloxy or cycloalkyloxy group.

The polymer or oligomer may be a conductive, semiconductive or insulating polymer. In particular, the polymer or oligomer may be a semiconductive polymer or oligomer. For example, the polymer or oligomer may be a high molecular weight polymer or oligomer. In particular, the polymer or oligomer may have a molecular weight greater than or equal to about 10,000 Da.

In contrast to a semiconductive polymer, a conductive polymer typically is heavily doped (>5 mol % by repeat unit) to a conductive state. As a result, a conductive polymer typically has a charge carrier concentration of $>10^{18}$ $cm^{-3}$. For the purposes of the present invention, a conductive polymer is a polymer having a conductivity $>10^{-5}$ S/cm. As such, their electrical properties are essentially insensitive to additional impurities. Such conductive polymers are useful mainly as transmission lines or electrode contacts. Crucially they often possess a transmission window that extends greatly over portions of the optical, ultraviolet and deep ultraviolet spectral regions, with increased laxity for photo-patterning processes.

Semiconductive polymers typically are undoped or intrinsically doped at a low concentration (typically 0.001 mol % or less). In contrast to a conductive polymer, a semiconductive polymer typically has a charge carrier concentration of $<10^{15}$ $cm^{-3}$. For the purposes of the present invention, a semiconductive polymer is a polymer having a conductivity $>10^{-8}$ S/cm. These polymers crucially form the core of a wide range of polymer device technologies including light emitting diodes (LED), field effect transistors (FET) and photovoltaic (PV) devices. The polymers typically have fairly narrow transmission windows in the optical-ultraviolet region as explained above. The polymers also have important and unique transport and photophysical properties that are far more sensitive to impurity levels.

Insulating polymers typically are undoped. In contrast to a semiconductive polymer, an insulating polymer typically has a charge concentration of $<10^{13}$ $cm^{-3}$. For the purposes of the present invention, an insulating polymer may be a polymer having a conductivity $<10^{-8}$ S/cm, preferably $<10^{-12}$ S/cm. Such insulating polymers are useful mainly as gate dielectric or isolation layers in wide range of polymer device technologies including field-effect transistors (FET) and in making heterostructure nanostructures.

The amount of cross-linking moiety comprised in the solution may be any suitable amount depending on the application of the cross-linking moiety. The cross-linking moiety may be present in an amount in the range of from 0.05 to 5 mol % based on the total weight of the polymer or oligomer and the cross-linking moiety in the solution. In particular, the cross-linking moiety may be present in the solution at a level in a range of from 0.05 to less than 5 mol %, 0.05 to 3 mol %, 0.1 to 2 mol %, 0.1 to 1 mol %, based on the total number of moles of the polymer or oligomer and the cross-linking moiety in the solution.

The solution according to the second aspect may be used in the manufacture of a polymer device.

According to a third aspect, there is provided a method for forming a polymer device comprising the steps of:

(a) depositing a solution comprising a polymer or oligomer and a cross-linking moiety on a substrate to form a layer; and (b) curing the layer to form an insoluble cross-linked polymer.

The polymer or oligomer and the cross-linking moiety may be as described above. The solution may be as described above. According to a particular aspect, the concentration of the polymer or oligomer in the solution may be 0.5 to 2.5 wt % before the addition of the cross-linking moiety.

The polymer or oligomer may comprise a backbone which may be at least partially conjugated. In particular, the polymer or oligomer backbone may be substantially or fully conjugated.

Referring to the structure of the polymer or oligomer, the polymer or oligomer may comprise a plurality of saturated hydrocarbon segments (—$CH_2$— and —CH—) in the side chain or main chain. In particular, the polymer or oligomer may comprise a plurality of aliphatic hydrogens. The weight fraction of the hydrocarbon segments in the polymer or oligomer may be 10-100%. In particular, for a semiconductive polymer, the weight fraction may be 10-70%.

The present method provides a simple route for cross-linking a polymer film post-deposition to obtain any desired film thickness, for example from about 1 nm to about 500 nm in one process cycle. In the present method, this can be achieved in a number of cases without introducing a significant concentration of charge-carrier traps or exciton traps. As a result, it is possible to fabricate a wide range of practical polymer-polymer heterostructures and incorporate them advantageously into polymer devices, particularly in light-emitting diodes, photodiodes and field-effect transistors.

Any suitable depositing process may be used for the purposes of the present invention. For example, the depositing step may be carried out by spin-casting, inkjet printing, screen-printing, dip coating, or flexographic printing the solution on the substrate.

Any suitable substrate may be used for the method of the present invention. The material of the substrate may depend on the polymer device being formed. For LEDs and photodiodes/photodetectors, the substrates may include a layer of ITO-on-glass, ITO-on-PET or ITO-on-Si. For FETs, the substrates may include a layer of glass, polyethylene terephthalate (PET) or polycarbonate. The substrate may comprise a laminate structure. The substrate may comprise a plurality of different layers.

Any suitable curing process may be used for the curing step of the method of the present invention. For example, the curing may be achieved by electron-beam radiation. The conditions under which the curing is carried out may comprise exposing the layer to short wavelength radiation in an inert atmosphere. The short wavelength radiation may be deep ultraviolet (UV). The wavelength of the deep ultraviolet radiation may be in the range 200-400 nm, 245-370 nm, 250-260 nm. In particular, the UV radiation may be about 254 nm or about 248 nm. The UV radiation may be obtainable from any suitable source. For example, the UV radiation may be obtainable from a Hg low-pressure lamp or a KrF excimer laser.

In particular, the cross-linking moiety may be sensitive to ultraviolet radiation having a wavelength in the range 200 nm to 400 nm. The curing may therefore comprise exposing the layer to UV radiation having a wavelength in the range 200 nm to 400 nm in an inert atmosphere. Where curing comprises exposing the layer to UV radiation this may be at a power of 1-100 mW/cm$^2$, and the exposure time may be in the range of about 0.1-100 s. The energy dose on the layer to be cured may be 1-100 mJ/cm$^2$. In particular, the energy dose may be 5-20 mJ/cm$^2$.

When the solution of the depositing step comprises oligomer, the curing step will polymerise as well as cross-link the oligomers to form the insoluble cross-linked polymer.

According to a particular aspect, a particular cross-linking moiety according to the present invention is mixed with a polymer or oligomer in solution. Cross-linking then proceeds via a mechanism in which the cross-linking reaction involves a bond-forming reaction between the cross-linking moiety and the polymer or oligomer units, as distinct from a bond-forming reaction between the cross-linking moieties themselves. In particular, during the curing step, the cross-linking moieties substantially do not self-couple or self-polymerise.

During the curing step, the layer formed in the depositing step may be rendered insoluble. To achieve this insolubility, a sufficient degree of cross-linking must occur during the curing step when the layer formed during the depositing step is subjected to cross-linking conditions. The precise amount, within the specified range, of cross-linking moiety needed in the solution that is deposited in the depositing step in order to achieve the required degree of cross-linking in the curing step will depend on the molecular weight distribution characteristics of the polymer. Generally, the higher the molecular weight of the polymer, the lower the amount of cross-linker that is needed. The minimum amount required suitably can be determined by a gel-fraction experiment. The experiment may be carried out by any suitable method. For example, the experiment may be as carried out by the steps described in WO 2004/100282.

The cross-linked polymer may be unconjugated, partially conjugated, substantially conjugated or fully conjugated. According to a particular aspect, the cross-linking moiety may be part of the main chain of the polymer or oligomer, or may be attached as a side chain to the polymer or oligomer.

The thicknesses for the cured layer formed in the curing step may be in the range of 500 nm or less. Where the curing step is by exposure to UV radiation, the insoluble layer formed may be from 500 nm thick down to few nm thick after one appropriate UV exposure. Layers where the final thickness is greater than 500 nm, where necessary, may be fabricated by repeated depositing and curing. The required final film thickness depends on end-use application. There is, in principle, no limit to the number of layers that may be fabricated by the method of the present invention.

The desired thickness of the insoluble layer formed in the curing step may be dependent, to some extent, on the function of the layer. Where the layer is an injection interlayer in a polymer LED, the preferred thickness may be in the range of from 5 to 20 nm. Where the layer is a charge-transport layer, in a photodiode for example, the thickness may be in the range of from 10 to 50 nm. Where the layer is a cladding layer in a waveguide device, the thickness may be in the range of from 100 to 400 nm. Where the layer is the channel layer in an FET, the thickness may be in the range of from 20 to 300 nm.

The layer deposited in step (i) may be a polymer blend or composite. Cross-linking may be used advantageously to increase the thermal stability of the cured polymer blend or composite or to optimise resistance of the final cured layer to solvent dissolution.

The layer is cured in the curing step so that the layer is rendered insoluble. This means that the layer, and thus, the polymer do not dissolve completely in any solvent that the layer would have dissolved in, prior to cross-linking. As mentioned above, achieving this result depends on achieving the required level of cross-linking for the particular layer in question. Generally, the cured layer is rendered insoluble in common organic solvents. Further, generally, the layer is rendered insoluble in aromatic hydrocarbon solvents, including, toluene, xylene, mesitylene, durene, hydronaphthalene, and halogenated solvents such as chloroform and chlorobenzene. These solvents are rendered useable in subsequent processing during device manufacture.

One specific test for determining insolubility may be described as follows:
  cast a film by spin coating or ink-jet printing and then curing;
  accurately measuring the thickness of the film by profilometry, ellipsometry or interferometry, call this $d_1$;
  soaking (or developing) the film for 10 s in a solvent that normally dissolves the polymer, then blow-drying or spin-off;
  measuring the film thickness a second time, call this $d_2$.

When the layer is totally "insoluble" there should be no decrease in film thickness after soaking the film/layer (i.e. $d_2/d_1=1.0$). In many instances, however, the layer only needs to be partially insoluble. Provided that the fraction retained ($d_2/d_1$) is known, any decrease can be allowed for in the design of the device. In general however, $d_2/d_1$ needs to be greater than 0.4, preferably greater than 0.5 to be useful.

After the curing step, the layer may be contacted with a solvent. The fact that the cross-linked polymer is insoluble in solvents in which an equivalent uncross-linked polymer would have been soluble means that the solvent with which the layer is contacted may be selected from a wide class of solvents including common organic solvents. This contact will not dissolve the cross-linked polymer that was formed in the curing step.

Optionally, after curing step, the layer may be washed with a suitable solvent. Such a washing step may be included where the layer is subjected in to patterned cross-linking in the curing step. This would involve exposing only selected areas of the layer from the depositing step to the curing conditions in the curing step. Any suitable process for exposing only the selected are may be used for the purposes of the present invention. This may be achieved for example by exposure to UV-radiation through a mask. Material in the exposed area will become insoluble whereas material in the unexposed area will remain soluble. This enables material in the unexposed area to be removed in the washing step.

Optionally, after the curing step, the layer may be chemically modified by suitable chemical reaction by wet chemistry. Such chemical reactions may include aromatic sulfonation, aminomethylation, or other derivatisation reactions.

Sulfonation introduces $SO_3H$ groups into a fraction of the polymer repeat units. This may be used to fabricate a self-doped conductive polymer layer. This particular reaction may be carried out under a wide variety of conditions. For example, by reacting the layer at $-60°$ C. with a dilute chloroform solution of chlorosulfonic acid.

Another reaction that may be useful is a methylation reaction of the NH groups introduced by the cross-linking reaction. This reaction will replace the hydrogen atom with a potentially more stable methyl group. This particular reaction may be carried out by reacting the layer at room temperature with methyl iodide, and then washing with triethylamine in a chloroform-ethanol mixture. Therefore after rendering the polymer layer insoluble, a variety of chemical reactions may be carried out to alter or tune the bulk properties and surface properties of the layers.

A further (second) layer may be deposited on the layer formed by the method of the present invention. In this regard, in view of the curing step, the layer formed in the method according to the present invention will not be soluble in any solution used to deposit a further (second) layer.

Optionally, the method according to the present invention may further include a step of annealing the insoluble polymer formed in the curing step. The annealing may be carried out under suitable conditions. The annealing may be carried out at a suitable temperature. In particular, the annealing may be carried out at a temperature in the range of $80\text{-}200°$ C. For example, the annealing may be carried out at $90°$ C. In particular, the annealing may be carried out at a temperature in the range of $120\text{-}200°$ C.

According to a particular aspect, a semiconductive polymer may be formed from the cross-linking moiety according to the present invention by any suitable method. For example, the semiconductive polymer may be photo-patterned or photo-crosslinked. In particular, a polymer solution is prepared with a suitable amount of the cross-linking moiety. The amount of cross-linking moiety to be added to the polymer solution may be selected from gel retention curves.

The gel retention curve is a gel curve of the film retention vs. the cross-linking moiety to polymer weight ratio (r) in the film. This can be achieved by preparing a series of solutions, in which r may be, for example, 0%, 0.25%, 0.5%, 1% or 2%. The solution is then photo-exposed and the film thickness is measured using a profilometer by making a scratch, developing and measuring the film thickness again at the same location of the same scratch. The ratio of the developed film thickness to the starting film thickness is the film retention. The plot of film retention against the weight ratio is the gel retention curve. The point on the gel retention where it takes off from the zero film retention is the gel point. This corresponds to the emergence of the first polymer chains of infinite molecular weight. Thereafter, the gel retention curve rises steeply for monodispersed polymers and more gently for broader molecular-weight distributions.

From the gel retention curve, the desired retention and required cross-linking moiety concentration is determined. According to a particular aspect, to obtain porous films, the film retention should not be less than about 60%.

Subsequently, the polymer solution comprising the cross-linking moiety is deposited onto a substrate using methods known to a skilled person. In particular, the polymer solution may be spin-cast or inkjet printed. The deposited film may be annealed at a suitable temperature under suitable conditions. For example, the film may be annealed at 90° C. for 5 minutes in $N_2$ to drive off solvent and redistribute the cross-linking moiety into the alkyl chain phase.

The film may be exposed by flood exposure or through a mask to deep UV at 254 nm in a glovebox. For example, the dose may be about 300 mJ/cm$^2$. The unexposed or uncross-linked materials are then removed by developing with solvent. For example, this may be done on a spinner by brief contact with a solvent and then spinning-off, or by dipping the substrate into a solvent bath. In this way, photo-patterning of polymer LEDs and FETs may be achieved.

The cross-linking moiety according to any aspect of the present invention has practically no effect on the photoluminescence and electroluminescence properties of a wide range of conjugated polymer films particularly when used in an amount in the range of from 0.1-0.5 mol % and when the molecular weight of the polymer is sufficiently high.

The cross-linking moiety and the method described above are compatible even with wide band-gap materials, in particular blue EL polymers, for example such as those described in WO 03/095586. The process does not introduce exciton or charge traps that would have otherwise impaired the device performance of these particularly sensitive materials.

The cross-linked polymer formed may be a conductive, semiconductive or insulating polymer. In particular, the cross-linked polymer may be a semiconductive polymer.

The cross-linking moiety does not generally suffer from the drawback of leaving residues that may interfere with the properties, such as charge-transport and luminescence properties, of the polymer. In particular, the π-π interaction between electron-rich organic semiconductor devices and electron-poor fluorophenyl azides is suppressed, and cross-links are more favourably allowed at the alkyl side chains.

The solid-state cross-linking efficiency for conjugated polymers is unexpectedly high with the cross-linking moiety according to the first aspect of the present invention. The high efficiency of the cross-linking moiety is due to the presence of fluorine atoms on the ring which suppresses a competing parasitic ring expansion side-reaction. The high efficiency is also due to the presence of the non-fluorine substituent in the ring which suppresses nitrene attack onto the π-conjugated backbone, and intermolecular charge transfer between the polymer and the cross-linking moiety, promoted by an undesirable quadrupolar interaction.

The polymer device formed in the method of the present invention may be an optical device. In particular, the device may be a polymer light emitting device such as a polymer light emitting diode (LED), a polymer transistor such as a field effect transistor (FET), a photodetector, a photovoltaic (PV) device, a waveguide device, or a distributed Bragg reflector. In particular, the polymer device may be a polymer waveguide LED device or a polymer microcavity LED device.

Polymer LED devices may be fabricated with a cross-linked hole-transport polymer layer deposited by the method of the present invention. The devices further may include a light-emitting polymer layer and/or electron-transport polymer layer and/or exciton-block polymer layer.

The further layers may be deposited as described in the depositing step of the method of the present invention. For polymer LEDs, one may for example conceive of a structure which comprises a hole-injecting and electron-blocking polymer layer formed on the anode, followed by the light-emitting polymer layer, and then an electron-injecting, hole-blocking and exciton-blocking polymer layer, followed by the cathode. Advantageously, appropriate polymers may also be patterned as the light-emitting layer to give a full colour display. In addition, the light-emitting layer may be a film of a cross-linked blend of polymers.

Polymer waveguide LED devices may be fabricated with one or more cross-linked polymer cladding layers deposited by the method of the present invention. The devices may further include a core light-emitting layer which optionally may be deposited in accordance with the present method. A waveguide device is characterised by a core layer (or strip) having a higher refractive index than the adjoining clad layers (or surrounding). The core layer and clad layers may each comprise one or more individual layers. Light of the appropriate wavelength that satisfies a phase-matching condition is trapped by total internal reflection and guided in the core layer (or strip) on account of its higher refractive index. This light can then be emitted at the edge of the device or guided to another region where it can be out-coupled. The light emitted in this way can be highly directional and also be well coupled to optical fibers.

Polymer distributed Bragg reflectors may be fabricated with cross-linked alternating high refractive index and low refractive index polymer multilayers deposited by the method of the present invention. A Bragg reflector comprises a plurality of quarterwave-thick ($d_H$, $d_L$) layers of high ($n_H$) and low ($n_L$) refractive index materials. Light of wavelengths that satisfy the Bragg condition ($\lambda/2 = n_H d_H + n_L d_L$) is strongly reflected within the stack. The Bragg reflector can be coupled with another Bragg reflector or mirror to form an optical resonator. Such resonators have important uses as wavelength selectors.

Polymer microcavity LED devices may be fabricated with one or more cross-linked polymer distributed Bragg reflector layers deposited by the method of the present invention. The devices further may include a core light-emitting layer. Optionally, the core light-emitting layer may be deposited in accordance with the present method.

Polymer FET devices may be fabricated with a cross-linked semiconductive polymer layer deposited by the method of the present invention. The devices further may include a cross-linked insulating polymer layer. Optionally, the insulating polymer layer may be deposited according to the present method. This is particularly if this layer is deposited before the semiconductive layer. The devices may be in top-gate, side-gate or bottom-gate configuration. For polymer FETs, one may for example conceive of a structure which comprises of a charge transporting semiconductive polymer formed on a substrate between source and drain electrodes, followed by an insulating polymer that acts as the gate insulator. This insulating polymer layer can be deposited from the same solvent system used to deposit the semiconductive polymer after the latter is cross-linked.

Polymer photovoltaic devices may be fabricated with a photoresponsive layer comprising a cross-linked polymer blend or polymer composite.

According to a fourth aspect of the present invention, there is provided a polymer device obtainable by the method as described above. The device may be as described above. In any of the devices described above, preferred materials for the cathode include alkali earth metals, such as barium and calcium.

Having now generally described the invention, the same will be more readily understood through reference to the following examples which are provided by way of illustration, and are not intended to be limiting.

EXAMPLES

Example 1—Ethylene bis(4-azido-2,3,5-trifluoro-6-methylbenzamide)

In a typical preparation, 1.00 g (5.15 mmol) of 2,3,4,5-tetrafluorobenzoic acid (1) in anhydrous THF (20 mL) was stirred and cooled to −78° C. 4.53 mL of BuLi (2.5 M in hexanes, 2.2 eq) was added drop wise. The resulting suspension was further stirred for 3 hours at −78° C. MEL (0.38 mL, 1.2 eq) in anhydrous THF (2 mL) was added drop wise, and the mixture stirred for another 0.5 hours, then warmed to room temperature, and stirred for a further 20 minutes whereupon a white suspension was obtained. The reaction was quenched by drop wise addition of deionised water, acidified and extracted by ethyl acetate (3×30 mL). The extract was dried with anhydrous MgSO$_4$, and evaporated to dryness at reduced pressure to give 6-methyl-2,3,4,5-tetrafluorobenzoic acid (2) as a white solid (yield=56%). 0.9 g of (2) was mixed with SOCl$_2$ (5 mL) and 1 drop of DMF, and heated at 75° C. for 12 hours. Excess SOCl$_2$ was removed at reduced pressure to give (3) as a yellowish oil and used without further purification. To a solution of 66.1 mg (1.1 mmol) of ethylenediamine and 0.4 mL of TEA in 5 mL of dry DCM, was added 0.5 g (2.2 mmol) of (3) in 5 mL of dry DCM. After stirring at room temperature for 10 hours, the reaction mixture was washed by brine (10 mL×3). The organic layer was dried over MgSO$_4$, and (4) was obtained after the solvent was removed as a white solid (yield=79%). A solution of 0.21 g of (4) and 0.31 g of NaN$_3$ (10 eq) in a mixing solvent (DMF 5 mL, H$_2$O 1.5 mL) was heated to 120° C. under dark condition for 10 hours. After being cooled down to room temperature, 10 mL water was added and the mixture was extracted by EA (3×15 mL). The extract was dried over MgSO$_4$ and the solvent was removed under reduced pressure. The crude product was further purified by chromatography on silica gel (EA:DCM=1:2) to give (5) as a white solid (yield 73%).

Example 2—Dodecylene bis(4-azido-2,3,5-trifluoro-6-methylbenzoate)

-continued

5

In a typical preparation, 1.00 g (5.15 mmol) of 2,3,4,5-tetrafluorobenzoic acid in anhydrous THF (20 mL) was stirred and cooled to −78° C. 4.53 mL of BuLi (2.5 M in hexanes, 2.2 eq) was added drop wise. The resulting suspension was further stirred for 3 hours at −78° C. MEL (0.38 mL, 1.2 eq) in anhydrous THF (2 mL) was added drop wise, and the mixture was stirred for another 0.5 hour. The mixture was then warmed to room temperature, and stirred for a further 20 minutes whereupon a white suspension was obtained. The reaction was quenched by drop wise addition of deionised water, acidified and extracted by ethyl acetate (3×30 mL). The extract was dried with anhydrous MgSO$_4$, and evaporated to dryness at reduced pressure to give (2) as a white solid (yield=56%). 0.9 g of (2) was mixed with SOCl$_2$ (5 mL) and 1 drop of DMF, and heated at 75° C. for 12 h. Excess SOCl$_2$ was removed at reduced pressure to give (3) as a yellowish oil and used without further purification. To a solution of 1,12-dodecanediol (0.145 g, 0.61 mmol) and triethylamine (0.16 mL, 1.2 mmol) in anhydrous dichloromethane (5 mL) was added (3) (0.33 g, 1.4 mmol, 15 mol % excess) dissolved in anhydrous dichloromethane (5 mL). The mixture was stirred at room temperature for 10 hours, then washed by brine (3×10 mL), dried over anhydrous MgSO$_4$ and evaporated to dryness at reduced pressure to give (4) as a colourless oil. This was purified by column chromatography (silica gel; eluting solvent, 2:1 hexane:dichloromethane) (yield=72%). (4) (0.30 g, 0.51 mmol) and NaN$_3$ (0.33 g, 5.1 mmol) were dissolved in a DMF:water mixture (7 mL:5 mL) and heated to 95° C. for 30 hours. Water (10 mL) was added and the mixture extracted by ethyl acetate (20 mL×3), dried over MgSO$_4$ and evaporated to dryness at a reduced pressure to give a yellow crude that was purified by column chromatography (silica gel; eluting solvent 2:1 hexane:dichloromethane) to give (5) as a white solid (yield=65%).

Example 3—Ethylene bis(4-azido-2,3,5-trifluoro-6-isopropylbenzoate)

-continued

In a typical preparation, 9.0 mL of isopropylchloride (98.4 mmol, 2.1 eq) was added drop wise to a mixture of 5 mL of 1,2,3,4-tetrafluorobenzene (46.6 mmol) and 1.24 g AlCl$_3$ (9.3 mmol, 0.2 eq). After stirring for 1 hour at room temperature, 10 mL of deionised water was added. The mixture was extracted by ether (3×20 mL). The extract was dried with anhydrous MgSO$_4$, and evaporated to dryness at reduced pressure to give 1-isopropyl-2,3,4,5-tetrafluorobenzene (1) as pale-yellow colour oil (yield=80.3%). To a solution of 3.0 g (15.6 mmol) of (1) in 25 mL of anhydrous THF was added 11 mL of n-BuLi (17.6 mmol, 1.6 M in hexanes, 1.13 eq) at −78° C. drop wise. The resulting suspension was stirred for 4 hours at −78° C. The resulting dark-blue coloured mixture was then poured into 100 g of dry-ice powder and stirred at room temperature for 1 hour. The mixture was acidified and extracted by EA (3×30 mL). The organic layer was dried over MgSO$_4$, and the solvent was removed under reduced pressure. (2) was obtained after the crude product was washed by hexane, as a white solid (yield=59%). The solution of 1.5 g of (2) and 5 mL of SOCl$_2$ (with 1 drop of DMF) was heated at 80° C. for 12 hours. (3) was obtained after the excess SOCl$_2$ was removed under reduced pressure as a yellowish oil, which was used for the next step without further purification. To a solution of 0.127 mL of ethylene glycol (2.31 mmol, 0.5 eq) and 0.646 mL of TEA (4.63 mmol) in 10 mL of dry DCM, was added 1.18 g (4.63 mmol) of (3) in 10 mL of dry DCM drop wise. After stirring at room temperature for 48 hours, the reaction mixture was washed by brine (3×30 mL). The organic layer was dried over MgSO$_4$ and the solvent was removed. The crude product was further purified by chromatography on silica gel (hexane:DCM=3:1) to give (4) as a colourless oil (yield=85%). A solution of 0.98 g of (4) and 1.0 g of NaN$_3$ (10.4 eq) in a mixing solvent (DMF 35 mL, H$_2$O 5 mL) was heated to 90° C. under dark conditions for 7 hours. After the reaction mixture was cooled down to room temperature, 20 mL of water was added and the mixture was extracted by EA (3×40 mL). The organic layer was dried over MgSO$_4$ and the solvent was removed under reduced pressure. The crude product was further purified by chromatography on silica gel (hexane:DCM=3:1) to give (5) as a colourless oil (yield=73%).

Example 4—Diethyleneoxy bis(4-azido-2,3,5-trifluoro-6-isopropylbenzoate)

As in Example 3, but with diethylene glycol replacing ethylene glycol. The product was a white solid (yield=90% at the last step).

Example 5—A Polymer with 1% of Side Chains Terminated with 4-azido-2,3,5-trifluoro-6-isopropylbenzoate 2,2'-(4,4,5,5-tetramethyl-1,3,2-dioxaborolane) diboronic ester of 9,9-dioctylfluorene (denoted as A) is co-polymerised with 2,2'-dibromo-9,9-dioctylfluorene (denoted as B) and 2,2'dibromo-9-octyl-9-ω-hydroxyoctylfluorene (denoted as B') in the relative mol ratio of 99:1 using the Suzuki coupling method. A 250 mL flask was charged with 1.50 g of A, and 0.999 mol eq of combined B+B', and 2.35 mol eq of PEG-PPG-PEG 4400 as emulsifier and 43 mL of toluene was degassed with N$_2$. 43.4 mg of tetrakis-(triphenylphosphine)-palladium (0.014 eq) was dissolved in 2 mL of degassed toluene and added into the mixture, followed by 8.04 mL (6 eq) of 2 M Na$_2$CO$_3$ solution, with rapid stirring to give a white emulsion. The rapidly stirred mixture was heated at reflux under N$_2$. After 3 days, the reaction was terminated by addition of 0.04 mL (0.2 eq) of bromobenzene, and refluxed with stirring for a further hour, before adding 0.06 g of phenyl boronic acid (0.2 eq) and refluxing for a further hour. The polymer was then precipitated in MeOH, and purified. To attach the cross-linking moiety, the polymer was dissolved in chloroform and reacted with 4-azido-2,3,5-trifluoro-6-isopropylbenzoyl chloride, and then purified by repeated precipitation by MeOH and re-dissolution in chloroform.

Example 6—Ethylene bis(4-azido-3,5-difluoro-2,6-diisopropylbenzoate)

In a typical preparation, 8.0 mL of isopropylchloride (88 mmol, 10.5 eq) was added drop wise to a mixture of 1 mL of 1-bromo-3,4,5-trifluorobenzene (8.4 mmol) and 0.22 g AlCl$_3$ (1.6 mmol, 0.2 eq) in an Argon charged vessel. After stirring for 2 hours at room temperature, 10 mL of deionised water was added. The mixture was extracted by ether (3×20 mL). The extract was dried with anhydrous MgSO$_4$, and evaporated to dryness at reduced pressure to give 1-bromo-3,4,5-trifluoro-2,6-diisopropylbenzene (1) as pale-yellow colour oil. To a solution of 7.38 g (25.0 mmol) of (1) in 100 mL of anhydrous THF was added 25 mL of n-BuLi (50 mmol, 2.0 M in cyclohexane, 2.0 eq) at −78° C. drop wise. The resulting suspension was stirred for 2 hours at −78° C. The resulting mixture was passed through a stream of dry carbon dioxide and stirred at room temperature overnight. The mixture was acidified by 50 mL of 5% HCl and THF was removed under vacuum. The crude product was extracted by DCM (4×50 mL). The organic layer was concentrated under vacuum and extracted with NaOH (5 g in 300 mL, 3×50 mL). The aqueous layer was acidified with 10% HCl (50 mL). The white precipitate was extracted with DCM. This organic layer was washed with deionised water (1×50 mL). DCM was removed under vacuum to give a white solid. The white solid was washed by warm deionised water (2×50 mL) and filtered. The purified solid was dissolved in DCM, dried over NaSO₄, and the solvent was removed under reduced pressure to give 3,4,5-trifluoro-2,6-diisopropylbenzoic acid (2) as white crystals (6.25 g, yield=96%). A solution of 7.38 g of (2) and 24 mL of SOCl₂ was refluxed at 90° C. for 8 hours in a dry Ar-charged vessel. (3) was obtained after the excess SOCl₂ was removed under reduced pressure as a yellow oil. It was dissolved in dry chloroform, followed by removal of chloroform and trace amounts of thionyl chloride. To a solution of 0.28 mL of ethylene glycol (0.31 g, 5.0 mmol, 0.4 eq) and 4.2 mL of TEA (30 mmol), was added 3.37 g (12.0 mmol) of (3) in a dry Ar-charged vessel. After stirring at 120° C. for 16 hours, the reaction mixture was cooled down to room temperature and dissolved in DCM. The solution was washed by 5% HCl (30 mL, stirred for 30 minutes) followed by water. The organic layer was dried over NaSO₄ and solvent was removed under reduced pressure. The crude product was further purified by chromatography on silica gel (hexane: DCM=3:1) to give (4) as colourless oil (yield=30%). A solution of 0.98 g of (4) and 1.0 g of NaN₃ (10.4 eq) was dissolved in DMSO (35 mL) and heated to 90° C. under dark conditions for 24 hours. After the reaction mixture was cooled down to room temperature, 20 mL water was added and the mixture was extracted by EA (3×40 mL). The organic layer was dried over NaSO₄ and the solvent was removed under reduced pressure. The crude product was further purified by chromatography on silica gel (hexane: DCM=3:1) to give (5).

Example 7—Diethyleneoxy bis(4-azido-3,5-difluoro-2,6-diisopropylbenzoate)

As in example 6, but with diethylene glycol replacing ethylene glycol.

Example 8—Ethylene bis(4-azido-3,5-difluoro-2,6-dihexylbenzoate)

In a typical preparation, 5.00 mL of n-Butyllithium (10 mmol, 2 eq) was added drop wise to a mixture of 0.60 mL of 1-bromo-3,4,5-trifluorobenzene (5 mmol) and 20 mL of dry tetrahydrofuran in an Argon-charged vessel at −78° C. After stirring for 1 hour at −78° C., 1.48 mL of iodohexane (10 mmol, 2 eq) diluted with 20 mL of tetrahydrofuran was added drop wise to the mixture. After stirring for a further 16 hours at −78° C., 10 mL of deionised water was added. The mixture was extracted by dichloromethane (3×20 mL). The extract was washed with brine (2×10 mL), dried with anhydrous MgSO₄, and evaporated to dryness at reduced pressure to give 1-bromo-3,4,5-trifluoro-2,6-dihexylbenzene (1) as pale-yellow coloured oil. To a solution of 1.9 g (5.0 mmol) of (1) in 20 mL of anhydrous THF was added 5 mL of n-BuLi (10 mmol, 2.0 M in cyclohexane, 2.0 eq) at −78° C. dropwise. The resulting suspension was stirred for 2 hours at −78° C. The resulting mixture was passed through a stream of dry carbon dioxide and stirred overnight at room temperature. The mixture was acidified by 20 mL of 5% HCl and THF was removed under vacuum. The crude product was extracted by DCM (3×20 mL). The combined organic layer was washed with brine (2×20 mL). DCM was removed under vacuum to give pale yellow oil. The pale yellow oil was purified through column chromatography on silica gel (DCM:Hexane=1:1). The solvent was removed through reduced pressure and 3,4,5-trifluoro-2,6-dihexylbenzoic acid (2) was obtained as a pale yellow oil. The solution of 1.72 g of (2) and 24 mL of SOCl₂ was refluxed at 90° C. for 8 hours in a dry Ar-charged vessel. (3) was obtained after the excess SOCl₂ was removed under reduced pressure. It was dissolved in dry chloroform, followed by removal of chloroform and trace amounts of thionyl chloride. To a solution of 0.28 mL of ethylene glycol (0.31 g, 5.0 mmol, 0.4 eq) and 4.2 mL of TEA (30 mmol), was added 4.35 g (12.0 mmol)

of (3) in a dry Ar-charged vessel. After stirring at 120° C. for 16 hours, the reaction mixture was cooled down to room temperature and dissolved in DCM. The solution was washed by 5% HCl (30 mL, stirred for 30 minutes) followed by deionised water (2×50 mL). The organic layer was dried over NaSO$_4$ and solvent was removed under reduced pressure. The crude product was further purified by chromatography on silica gel (hexane:DCM=3:1) to give (4). A solution of 1 g of (4) and 0.91 g of NaN$_3$ (10 eq) was dissolved in DMSO (35 mL) and heated to 90° C. under dark conditions for 24 hours. After the reaction mixture was cooled down to room temperature, 20 mL water was added and the mixture was extracted by EA (3×40 mL). The organic layer was dried over NaSO$_4$ and the solvent was removed under reduced pressure. The crude product was further purified by chromatography on silica gel (hexane:DCM=3:1) to give (5).

Example 9—Diethyleneoxy bis(4-azido-3,5-difluoro-2,6-dihexylbenzoate)

As in example 8, but with diethylene glycol replacing ethylene glycol.

Example 10—Comparative Example

Figure 1:
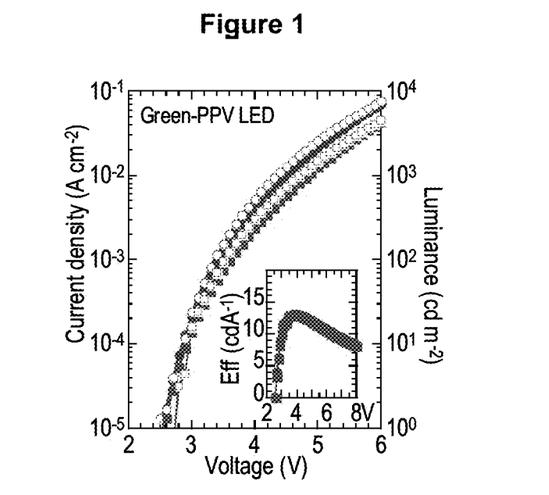
FIG. 1: Current-voltage-luminance characteristics of green-PPV LEDs comprising ethylene bis(4-azido-2,3,5-trifluoro-6-isopropylbenzoate) as the cross-linking moiety (square symbol) at a cross-linking density of $7 \times 10^{18}$ cm$^{-3}$ compared with control devices without cross-linking moieties (circle symbols) and DUV exposure.
Figure 2:
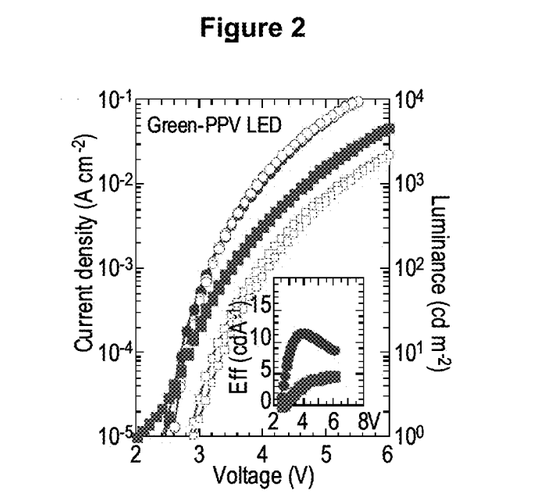
FIG. 2: Current-voltage-luminance characteristics of green-PPV LEDs comprising ethylene bis(4-azido-2,3,5,6-tetrafluorobenzenesulfonamide) as the cross-linking moiety (square symbol) at a cross-linking density of $7 \times 10^{18}$ cm$^{-3}$ compared with control devices without cross-linking moieties (circle symbols) and DUV exposure.

Light-emitting diodes based on a phenyl-substituted poly (p-phenylenevinylene) green light-emitting polymer were fabricated in which the light-emitting layer was cross-linked by ethylene bis(4-azido-2,3,5-trifluoro-6-isopropylbenzoate) according to Example 3 above (FIG. 1) or ethylene bis(4-azido-2,3,5,6-tetrafluorobenzenesulfonamide) as prepared in WO 2004/100282 (FIG. 2). The device structure comprised indium-tin-oxide glass, spin-coated with 50-nm thick poly(3,4-ethylenedioxythiophene)-poly(styrenesulfonate) layer, 80-nm-thick phenyl-substituted poly(p-phenylenevinylene) with identical cross-linker concentration of 7×10$^{18}$ cm$^{-2}$. The film was exposed to deep ultraviolet in a nitrogen glove box for 2 minutes to give a dose of 300 mJ/cm$^2$ at 254 nm wavelength. The diodes were then completed by evaporation of 30-nm-thick Ca cathode followed by 120 nm thick Al capping layer. The open symbols in the figures give the luminance while the solid symbols in the figures give the current. The data for the device without the cross-linking moiety, which is used as the control for comparison, is given as circle symbols. The data for the device with the cross-linking moiety is given as square symbols.

The data clearly shows that there is no change in the electroluminescence efficiency for the device with ethylene bis(4-azido-2,3,5-trifluoro-6-isopropylbenzoate) as the cross-linking moiety (see inset of FIG. 1), but the electroluminescence efficiency decreases by a factor of two when ethylene bis(4-azido-2,3,5,6-tetrafluorobenzenesulfonamide) is the cross-linking moiety (see inset of FIG. 2). In both cases, the current densities are substantially unchanged from the diodes without cross-linking moieties.

The invention claimed is:

1. A cross-linking compound having a general formula II:

(Ar$_F$-W)$_n$-L    (II), wherein:
n is an integer greater than or equal to 2;
each Ar$_F$ is the same or different and comprises a fluorinated phenyl azide group having at least one non-fluorine containing substituent that is bulkier than fluorine at a meta position relative to the azide group, the at least one non-fluorine containing substituent is selected from a group consisting of a substituted or unsubstituted: alkyl, cycloalkyl, alkoxy and cycloalkoxy groups;
W comprises an electron-withdrawing group; and
L comprises a linker group, wherein two or more units of (Ar$_F$-W) are linked together by L, provided that the compound of general formula II is not ethylene bis(4-azido-2,3,5-trifluoro-6-isopropylbenzoate).

2. The cross-linking compound according to claim 1, wherein the non-fluorine containing substituent is a substituted or unsubstituted alkyl group with an alkyl chain length of from 1 to 18 carbon atoms.

3. The cross-linking compound according to claim 1, wherein the non-fluorine containing substituent is a substituted or unsubstituted alkyl group, where the alkyl group is a linear or branched alkyl group.

4. The cross-linking compound according to claim 1, wherein the non-fluorine containing substituent is a substituted or unsubstituted alkyl group selected from the group consisting of methyl, ethyl, iso-propyl, secondary butyl, tertiary-butyl, hexyl, octyl, and branched derivatives thereof.

5. The cross-linking compound according to claim 1, wherein W is in the para position relative to the azide group.

6. The cross-linking compound according to claim 1, wherein W comprises a sulfonyl group or a carbonyl group.

7. The cross-linking compound according to claim 6, wherein W comprises an electron-withdrawing group selected from the group consisting of: —CO—, —C(O)O—, —S(O$_2$)O—, —C(O)N—, and —S(O$_2$)N—.

8. The cross-linking compound according to claim 1, wherein L comprises a divalent or multivalent linker group selected from the group consisting of substituted or unsubstituted: alkyldioxy, alkyltrioxy, alkyldiamide, alkyltriamide and dialkyltrioxy.

9. The cross-linking compound according to claim 8, wherein L is selected from the group consisting of: ethylenedioxy, ethylenediamide, diethylenetrioxy and 1,3,5-trioxycyclohexane.

10. The cross-linking compound according to claim 1, wherein the cross-linking compound is selected from the group consisting of:
ethylene bis(4-azido-2,3,5-trifluoro-6-methylbenzamide);
dodecylene bis(4.azido-2,3,5-trifluoro-6-methylbenzoate);
ethylene bis(4-azido-3,5-difluoro-2,6-diisopropylbenzoate);
ethylene bis(4-azido-3,5-difluoro-2,6-dihexylbenzoate);
diethyleneoxy bis (4-azido-3,5-difluoro-2,6-diisopropylbenzoate); diethyleneoxy bis(4-azido-2,3,5-trifluoro-6-isopropylbenzoate); and
diethyleneoxy bis(4-azido-3,5-difluoro-2,6-dihexylbenzoate).

11. The cross-linking compound according to claim 1, wherein the cross-linking compound has a formula:

Ar$_F$-W-L-W-Ar$_F$.

12. A solution comprising the cross-linking compound moiety according to claim 1.

13. The solution according to claim 12, further comprising a polymer or oligomer.

14. The solution according to claim 13, wherein the polymer or oligomer is a semiconductive polymer or oligomer.

15. A method of forming a polymer device comprising the steps of:

(a) depositing a solution comprising a polymer or oligomer and a cross-linking compound according to claim 1, on a substrate to form a layer; and (b) curing the layer formed in (a) to form an insoluble cross-linked polymer.

16. The method according to claim 15, wherein the cross-linking compound is sensitive to ultraviolet radiation having a wavelength in the range 200 nm to 400 nm and the curing comprises exposing the layer to UV radiation having a wavelength in the range 200 nm to 400 nm in an inert atmosphere.

17. The method according to claim 15, wherein the cross-linked polymer is unconjugated, partially conjugated, substantially conjugated or fully conjugated.

18. The method according to claim 15, further comprising annealing the cross-linked polymer.

19. The method according to claim 15, wherein the polymer device is selected from the group consisting of: a polymer LED device, a polymer distributed Bragg reflector, a polymer FET device, a polymer photodetector and a polymer photovoltaic device.

20. The method according to claim 19, wherein the polymer device is a polymer waveguide LED device or a polymer microcavity LED device.

* * * * *